US008054984B2

(12) United States Patent
Klossowski

(10) Patent No.: US 8,054,984 B2
(45) Date of Patent: Nov. 8, 2011

(54) SOUND ALTERING APPARATUS

(75) Inventor: Uwe Klossowski, New Bern, NC (US)

(73) Assignee: BSH Home Appliances Corporation, Huntington Beach, CA (US)

( * ) Notice: Subject to any disclaimer, the term of this patent is extended or adjusted under 35 U.S.C. 154(b) by 1423 days.

(21) Appl. No.: 11/581,904

(22) Filed: Oct. 16, 2006

(65) Prior Publication Data

US 2008/0089528 A1 Apr. 17, 2008

(51) Int. Cl.
*A61F 11/06* (2006.01)
*G10K 11/16* (2006.01)
*H03B 29/00* (2006.01)

(52) U.S. Cl. .................... 381/71.3; 381/71.2; 381/71.14

(58) Field of Classification Search ................. 381/71.3, 381/71.2, 71.1, 71.14, 71.8, 114, 94.3, 94.6, 381/98, 100; 134/183, 184, 201
See application file for complete search history.

(56) References Cited

U.S. PATENT DOCUMENTS 4,166,197 A * 8/1979 Moog et al. .................. 381/101
5,129,003 A * 7/1992 Saruta .......................... 381/71.3
5,410,607 A * 4/1995 Mason et al. ................ 381/71.2
5,692,053 A 11/1997 Fuller et al.
6,075,308 A 6/2000 Date
6,178,246 B1 1/2001 Bebesel et al.
6,654,467 B1 * 11/2003 York et al. ................. 381/71.14
6,768,799 B1 * 7/2004 Thomas ....................... 381/71.3
2005/0226435 A1 10/2005 Steer

FOREIGN PATENT DOCUMENTS

DE 39 16 031 12/1989
DE 39 16 032 12/1989
DE 198 36 483 2/2000
WO 9311529 A1 6/1993

OTHER PUBLICATIONS

National Search Report DE 10 2006 060 033.9.

* cited by examiner

*Primary Examiner* — Xu Mei
(74) *Attorney, Agent, or Firm* — James E. Howard; Andre Pallapies

(57) ABSTRACT

A sound altering apparatus for altering predetermined sound levels of a sound producing device, the sound altering apparatus includes at least one piezoelectric foil sensor disposed relative to the sound producing device with the at least one piezoelectric foil sensor being operable to convert such sound wave energy into an electric sound signal one or more electric circuits in electrical communication with the at least one piezoelectric foil sensor for receiving the electric sound signal and shunting the electric sound signal to a ground connection, or to produce cancelling sound wave energy in the vicinity of the sound producing device, thereby reducing sound heard outside the sound producing device.

8 Claims, 4 Drawing Sheets

SOUND ALTERING APPARATUS

BACKGROUND OF THE INVENTION

The present invention is directed broadly to apparatus for altering sound energy emitted from appliances for residential and commercial settings and, more particularly, to an apparatus for altering sound energy in a manner that reduces such sound energy in the form of noise produced during the operation of residential or home appliances.

Large household appliances such as dishwashers, refrigerators, laundry machines, including washers and dryers, and even smaller household appliances such as oven hood vent fans, wine coolers, espresso-making apparatus, food mixers, food processors, juice centrifuges, juice extractors, and waste masticators all emit a certain amount of sound in the form of noise in connection with the operation of fans, electric drive motors, pumps, compressors, or other customary components of such appliances. Such sound emissions may be objectionable as noise to some and to others may just appear as loud sound energy. The use and accommodation of such appliances within residences and other settings would be improved if there existed a capability to selectively alter the sound level including altering the sound level to a reduced (lower decibel) level.

To that end, much time and effort has already been expended in providing insulation for sound producing components of such appliances, in providing more balancing of such sound producing components, and in more efficiently using electricity so as to reduce the emitted noise. The insulation helps to reduce the noise heard outside of the sound producing device and, indeed, much progress has been made in reducing noise from household appliances. On the other hand, it is generally understood that to further lower noise or sound emissions from these appliances would be desirable and will in fact advance the desired goal of full seamless integration of such appliances into the full range of residential and commercial settings. It would therefore be desirable if other methods and apparatus beyond the known insulation, balancing, and energy efficiency approaches were available to help reduce the sound level emitted from such sound producing home appliances.

SUMMARY OF THE INVENTION

To that end, it is an object of the present invention to provide a sound altering apparatus for altering predetermined sound levels from a sound-producing device such as a home appliance, wherein the sound altering apparatus provides efficient sound reduction for a relatively low cost.

It is another object of the present invention to electronically monitor the sound energy emitted from the sound-producing elements of such household machinery and, in turn, electronically cancel the noise.

To those ends, the present invention provides several embodiments of a sound altering apparatus. According to one embodiment of the present invention, there is provided a sound altering apparatus for altering predetermined sound levels of a sound producing device. The sound altering apparatus includes at least one piezoelectric foil sensor disposed relative to the sound producing device such that the at least one piezoelectric foil sensor is influenced by sound wave energy emitted from the sound producing device with the at least one piezoelectric foil sensor being operable to convert such sound wave energy into an electric sound signal. The present invention further includes an electric circuit in electrical communication with the at least one piezoelectric foil sensor for receiving the electric sound signal, the electric circuit including a ground connection and being configured for shunting the electric sound signal to the ground connection, thereby reducing sound heard outside the sound producing device.

The electric circuit off the present invention may also include at least one resistor for dissipating at least a portion of the electric sound signal as heat. Further, the present invention may include an array of piezoelectric foil sensors disposed at spaced intervals relative to the sound producing device.

According to one aspect of the present invention, the sound producing device may be a dishwasher having a pump, and the at least one piezoelectric foil sensor is disposed relative to the pump such that the at least one piezoelectric foil sensor is influenced by sound wave energy emitted from the pump. In addition the sound producing device may be a dishwasher having a pump and a dishwashing compartment with the array of piezoelectric foil sensors including at least one sensor disposed within the sound producing device for sensing pump sound and at least one other sensor disposed adjacent the dishwashing compartment for sensing sound produced by water circulating within the dishwashing compartment.

The sound altering apparatus of the present invention is adaptable to several home appliances. These may include a selected one of a dishwasher, a clothes washer, a clothes dryer, a refrigerator, a ventilation device, a wine cooler, an espresso making apparatus, a food mixing machine, a food processor, a juice centrifuge, a juice extractor and a waste masticator. Here, the at least one piezoelectric foil sensor is influenced by sound wave energy emitted from the selected sound producing device with the at least one piezoelectric foil sensor being operable to convert such sound wave energy into the electric sound signal.

According to another embodiment, the present invention is directed to a sound altering apparatus for altering predetermined sound levels of a sound producing device, the sound altering apparatus and including at least one piezoelectric foil sensor disposed relative to the sound producing device for sensing sound wave energy emitted therefrom and converting the sound wave energy to an electric sound signal. Also included is a first electric circuit in electrical communication with the at least one piezoelectric foil sensor for receiving and analyzing the electric sound signal to determine audible frequencies that characterize the sound, and generating a first electric signal representative thereof, the electric circuit including a ground connection and being configured for shunting the at least a portion of the electric sound signal to the ground connection. In addition to the first electrical circuit, this embodiment of the present invention includes a second electric circuit including a frequency processor and generator in electrical communication with the first electric circuit for receiving the first electric signal and generating a second electric signal representative of sound cancelling frequencies. Further, a third electric circuit is provided in electrical communication with the second electric circuit and including a sound transducer disposed in audible communication with the sound generating device, the third electrical circuit being configured for receiving and processing the second electrical signal to produce sound cancelling sound waves using the sound transducer, thereby reducing sound heard outside the sound producing device.

The first electric circuit may include at least one resistor for dissipating at least a portion of the first electric signal as heat. In addition the present invention may include an array of piezoelectric foil sensors disposed at spaced intervals relative to the sound producing device.

According to one aspect of the present invention, the sound producing device may be a dishwasher having a pump, and the at least one piezoelectric foil sensor is disposed relative to the pump such that the at least one piezoelectric foil sensor is influenced by sound wave energy emitted from the pump. Further, the array of piezoelectric foil sensors may include at least one sensor disposed relative to the sound producing device for sensing pump sound and at least one sensor disposed relative to the dishwashing compartment for sensing sound produced by water circulating within the dishwashing compartment.

The second embodiment of the present invention is also adaptable to many home appliances. These may include a dishwasher, a clothes washer, a clothes dryer, a refrigerator, a ventilation device, a wine cooler, an espresso making apparatus, a food mixing machine, a food processor, a juice centrifuge, a juice extractor and a waste masticator and the at least one piezoelectric foil sensor is influenced by sound wave energy emitted from the selected sound producing device with the at least one piezoelectric foil sensor being operable to convert such sound wave energy into the electric sound signal.

The present apparatus can be configured to operate in coordination with different modes of operation of the host appliance. According to another embodiment of the present invention, a sound altering apparatus for altering predetermined sound levels of a sound producing device, the sound altering apparatus includes at least one piezoelectric foil sensor disposed relative to the sound generating device for sensing sound wave energy emitted therefrom and converting the sound wave energy to an electric signal. The present invention further includes a first electric circuit in electrical communication with the at least one piezoelectric foil sensor for receiving and analyzing the electric sound signal to determine audible frequencies that characterize the sound and generating a first electric signal representative thereof; and a second electrical circuit including a frequency processor and generator in electrical communication with the first electric circuit for receiving the first electric signal and generating a second electric signal representative of sound cancelling frequencies. Also provided is a third electric circuit in electrical communication with the second electrical circuit and including a sound transducer disposed in audible communication with the sound generating element, the third electrical circuit being configured for receiving and processing the second electrical signal to produce sound cancelling sound waves using the sound transducer. This embodiment of the present invention also includes a control circuit in electrical communication with the third electrical circuit for controlling operation thereof, the control circuit having at least two selectively engagable operational modes including a first mode for real-time monitoring of the second electrical signal for controlling the third electrical circuit responsive thereto, and a second mode for operating the third electrical circuit in conjunction with predetermined operational modes of the sound producing device, thereby reducing sound heard outside the sound producing device.

The apparatus of the present invention may also include an array of piezoelectric foil sensors disposed at spaced intervals relative to the sound generating device.

As with the other previously addressed embodiments, the present invention may include a dishwasher having a pump and the at least one piezoelectric foil sensor is disposed relative to the sound producing device for sensing pump sound. Further, the present invention may include a dishwasher having a pump and a dishwashing compartment with the array of piezoelectric foil sensors including at least one sensor disposed relative to sound producing device for sensing pump sound and at least one sensor disposed relative to the dishwashing compartment for sensing sound produced by water circulating within the dishwashing compartment.

In accordance with prior-discussed embodiments, the sound generating element may be associated with a device selected from the group consisting of a dishwasher, a clothes washer, a clothes dryer, a refrigerator, a ventilation device, a wine cooler, an espresso making apparatus, a food mixing machine, a food processor, a juice centrifuge, a juice extractor and a waste masticator and the at least one piezoelectric foil sensor is influenced by sound wave energy emitted from the selected sound producing device with the at least one piezoelectric foil sensor being operable to convert such sound wave energy into the electric sound signal.

The present invention is adaptable in to various appliances in increasing levels of complexity and provides sound altering capabilities beyond those attainable with known insulation, balancing, and energy efficiency approaches alone.

DESCRIPTION OF THE PREFERRED EMBODIMENTS

Turning now to the drawings and, more particularly to FIG. 1, there is illustrated in a front plan view in partial section, a dishwasher 10, it being noted that this dishwasher 10 is hereinafter described as an exemplarily appliance having sound producing components disposed therein and which is amenable to be configured with an embodiment of the sound altering apparatus of the present invention to favorable alter the noise characteristics of the dishwasher. It should also be noted that the sound altering methods and apparatus applied with respect to the present dishwasher 10 are equally applicable to other sound producing items including, but not limited to, a clothes washer, a clothes dryer, a refrigerator, a ventilation device such as a range hood, a wine cooler, an espresso making apparatus, a food mixing machine, a food processor, a juice centrifuge, a juice extractor and a waste masticator. All these items have some form of sound producing apparatus or device in common. It should be apparent to those skilled in the art that the sensors, as will be explained in greater detail hereinafter, should be placed strategically in the area of the sound producing element within the device so that they may sense the sound emitted therefrom.

Additionally, it is noted that the present invention is operable to reduce sound energy that may be described as “noise” heard outside the housing or container of one of the aforesaid appliances or any other appliance that may be adaptable to such technology. Herein, when discussing noise, a certain amount of subjectivity is involved in that the term noise generally indicates a harsh or unpleasant sound. The present invention is configured for reducing sound in general and basically is intended to alter the sound emitted from appliances. Accordingly, while such sound alteration may not amount to noise reduction according to some listeners, such sound alteration when referred to as noise reduction should not be considered beyond the scope and spirit of the present invention.

Figure 1:
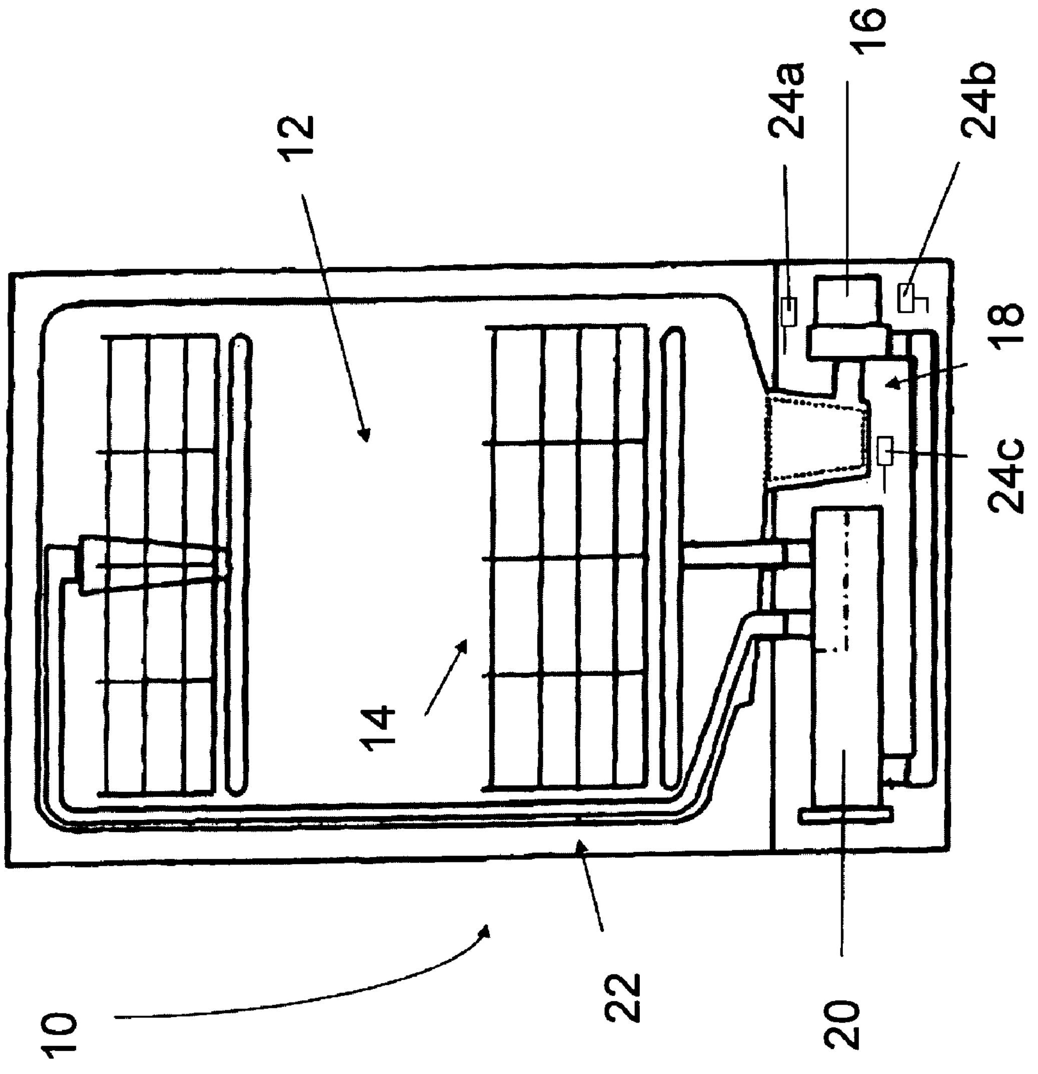
FIG. 1 is a front plan view, in partial section, of a dishwasher configured with one preferred embodiment of the present invention.

With continued reference to FIG. 1, a dishwasher 10 includes a washing compartment 12 containing one or more racks 14 for holding dishes or other household items to be cleaned. Water is driven through the dishwasher 10 by a pump 16 disposed underneath the washing compartment 12 in a pump housing or area 18, which may or may not be isolated structurally from the washing compartment 12. The particular dishwasher 10 illustrated includes a flow heater 20 that receives water from the pump 16 and delivers the heated water into the washing compartment 12 through water lines 22. As may be expected, noise may be generated by the pump 16, the flow heater 20, water flowing through the water lines 22 as well as water bombardment within the washing compartment 12. Even though components such as the pump 16 are chosen and mounted within the dishwasher 10 in a manner designed to reduce noise, noise or sound heard outside of the appliance is not completely eliminated.

According to the one preferred embodiment of the present invention, piezo foil sensors 24*a*, 24*b* and 24*c* are placed within the pump housing 18 in an area adjacent the pump 16 or in an area sufficient that they receive sound wave energy from the pump 16. According to one basic version of the present invention, the piezo foil sensors 24*a*, 24*b* and 24*c* are connected to ground in order to shunt the sound signal to ground. The piezo foil sensors 24*a*, 24*b* and 24*c* may alternatively be configured of a ceramic material.

Figure 2:
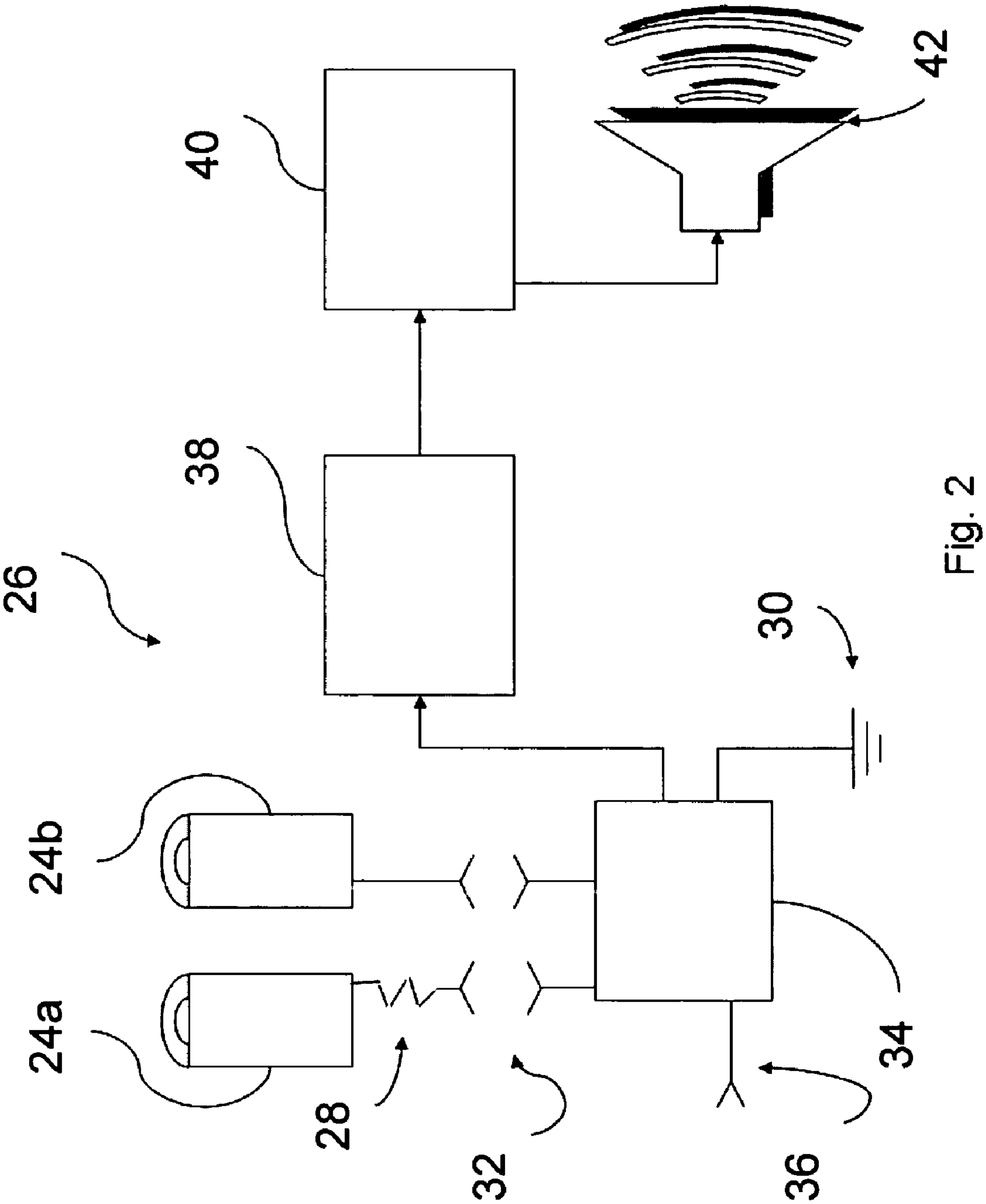
FIG. 2 is a diagrammatic view of an electrical circuit of the present invention according to a further preferred embodiment thereof.

The piezo foil sensors receive sound wave energy and are vibrated thereby. As with any piezo-based device, such vibrations are converted to electrical energy by the piezo device. As seen in FIG. 2 in which a further preferred embodiment of the sound altering apparatus of the present invention is illustrated, the sound altering apparatus of the present invention, hereinafter designated as the sound altering apparatus 26, includes a resistor 28 that may be placed in the circuit intermediate a piezo foil sensor (here, for illustration purposes the sensor illustrated at 24*a*) and a ground connection 30 to dissipate some of the electrical energy generated by the piezo foil sensor as heat.

With continued reference to FIG. 2, the sound altering apparatus 26 also includes an array of sensors 24*a*, 24*b* connected through wiring and associated connectors 32 to a filter 34. The filter 34 is supplied with a base current 36 for operational purposes associated with the electronic components therein as necessary. Optionally, the filter 34 may be switchable to provide both a passive and an active noise reduction, as necessary based on the sound producing device in question. The filter 34 acts to filter out certain frequencies, sound levels or both from the signal received from the sensors 24*a*, 24*b* and shunt that noise to ground through the ground connection 30. The filter may also pass other noise or sound signals to a frequency processor 38. The frequency processor 38 processes the sound signal received from the filter 34 to define the predominant sound levels and frequencies in the filtered signal for removal and delivers its signal to a frequency generator 40 that will cancel certain frequencies based on the input signal from the frequency processor. The frequency processor 38 may be optionally provided or not provided depending upon operational requirements apparent to those skilled in the art and may include amplifiers and filters as necessary to provide a workable signal that the frequency generator 40 can use to produce cancellation signals.

The frequency generator produces and emits signals at a frequency that, when combined with the noise signals, produce nodes where there was once peak noise and delivers such frequency cancellation signals to a sound transducer 42 that may be a speaker disposed sufficiently adjacent to the noise emitting device so as to produce cancelling soundwaves which interact with the noise sound energy within the sound producing device to reduce noise heard outside the sound producing device.

Figure 3:
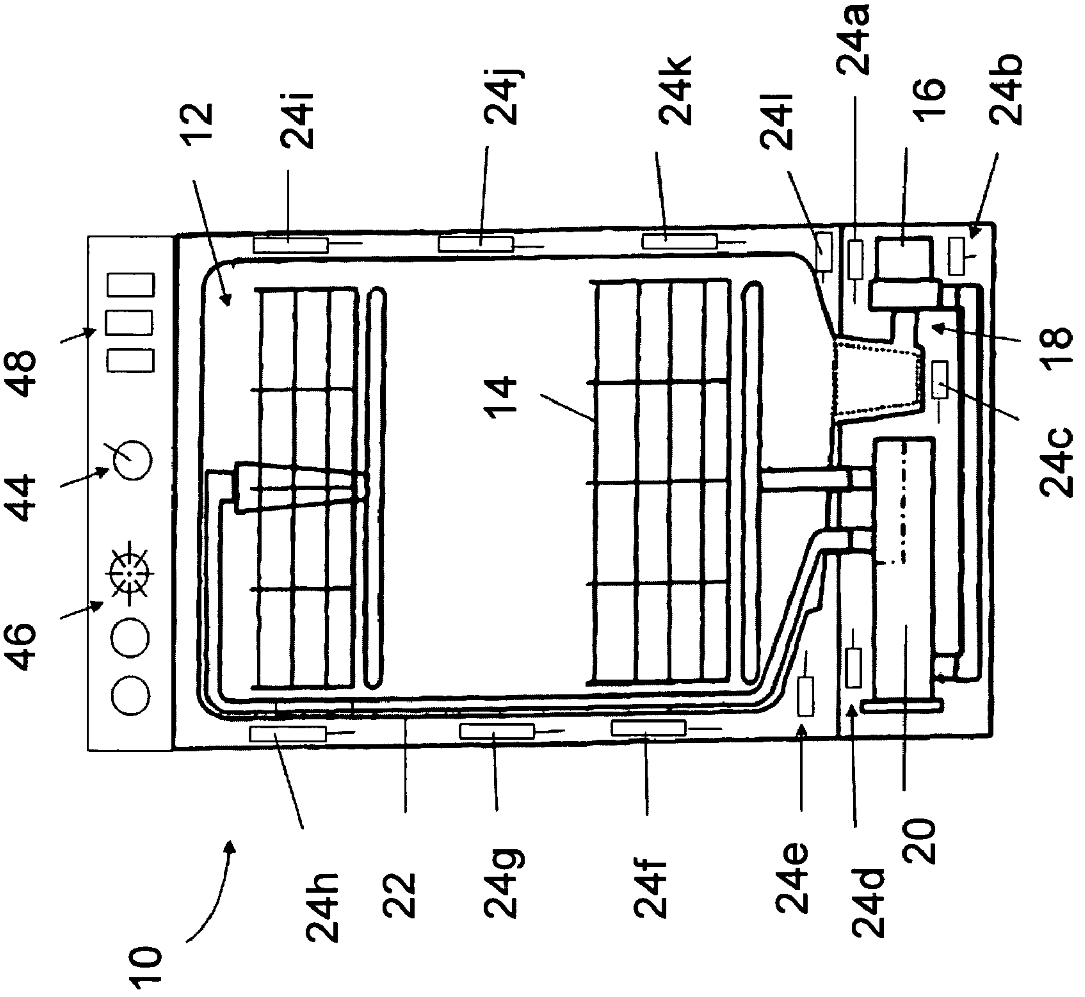
FIG. 3 is a front plan view, in partial section, of a dishwasher configured with another preferred embodiment of the present invention.

With reference now to FIG. 3, the dishwasher 10 is shown configured with another preferred embodiment of the sound altering apparatus of the present invention has been equipped with an array of piezo foil sensors 24*a*, 24*b*, 24*c*, 24*d*, 24*e*, 24*f*, 24*g*, 24*h*, 24*i*, 24*j*, 24*k*, and 24*l* disposed strategically in areas of motor noise, flow noise, and other vibrational noise in order to receive and convert a substantial amount of the sound energy waves produced by the device to electric current for feeding to processing circuitry such as has been described with respect to the sound altering apparatus 26.

The present invention is adaptable for use in a real time monitoring mode or may be coordinated with the respective appliance to operate during different modes of operation of the appliance. For example, and with reference to FIG. 3, the dishwasher 10 may include a wash cycle, a rinse cycle, and a drying cycle. The wash and rinse cycles could, depending on the internal structure of the dishwasher, produce a level of noise discernible to a house occupant in the vicinity of the dishwasher. The drying cycle with no moving water would produce very little, if any, such discernible sound energy. For clarity, the dishwasher 10 is illustrated with a selector switch 44, indicator lights 46, of which one indicator light is illuminated, and basic control switches 48.

Figure 4:
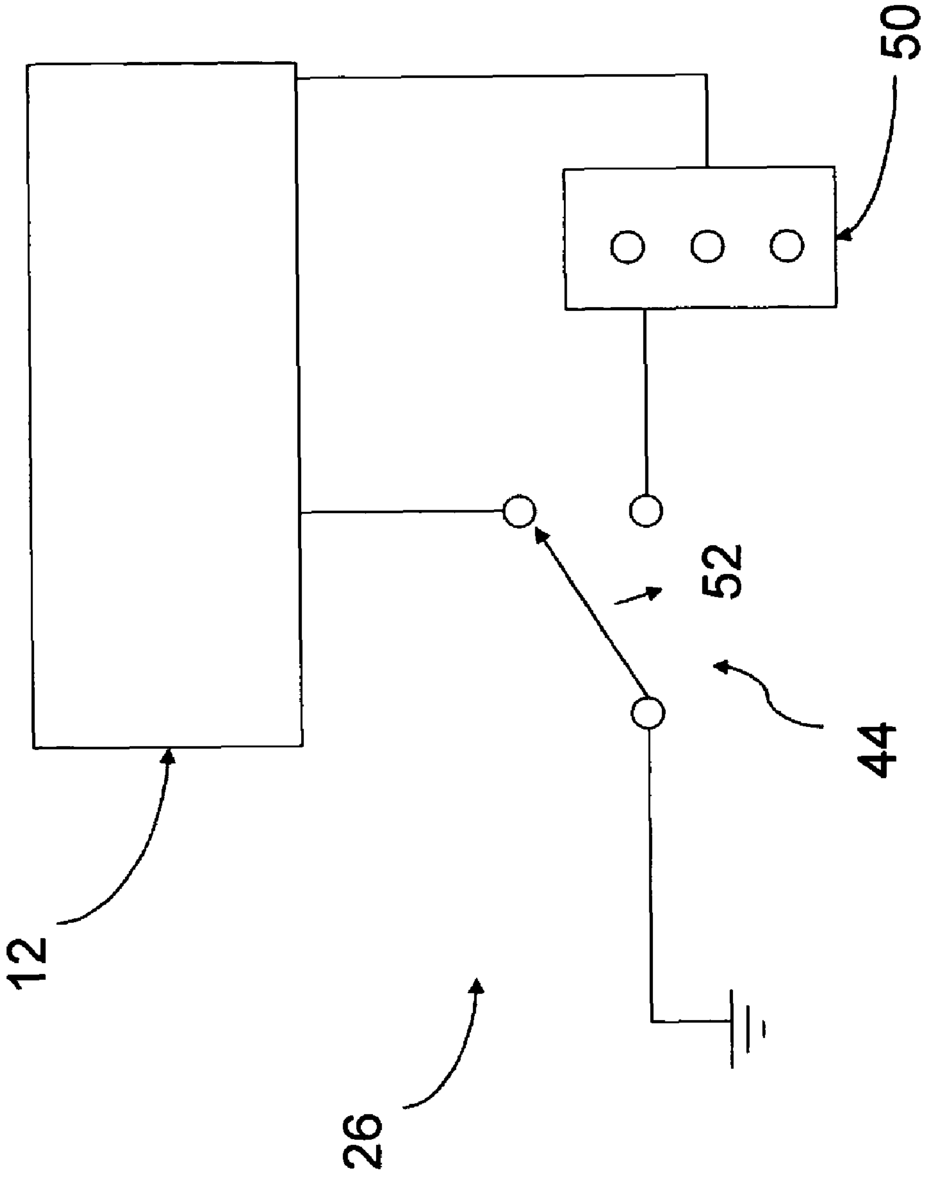
FIG. 4 is a diagrammatic view of another electrical circuit according to an additional preferred embodiment of the present invention.

With reference to FIGS. 3 and 4, when the switch 44 is in a first position, as seen in FIG. 4, the real time monitoring mode is engaged and the piezo foil elements and associated circuitry are fully operational at all times. If the switch is moved in the direction shown by the arrow 52 in FIG. 4 to its second position (not shown), its operation becomes dependent upon the mode of operation currently being performed within the washing compartment 12 of the dishwasher 10. Such mode circuitry is illustrated generally at 50. It will be apparent to those skilled in the dishwasher control electronics art that the present invention is easily adaptable to such control circuitry for choosing the operational mode of the sound altering apparatus 26 of the present invention in light of the operational mode of the dishwasher 10.

In operation and with reference to FIGS. 3 and 4, an operator may select the real time or coordinated mode using the selector switch 44. If the real time mode is chosen, the sensors 24*a*-24*l*, as seen in FIG. 3 are in constant operation so long as the dishwasher is operational as selected by the basic control switches 48. If the coordinated mode is chosen using the selector switch 44, operation of the present apparatus is ongoing in coordination with the dishwasher operational modes.

Whatever the selection, when the present apparatus is active, the sensors 24*a*-24*l* receive sound pressure waves from the noise generating components and are excited thereby to convert the sound pressure wave energy into an electric current, known herein as a sound signal. The sound signal is fed to a filter where a portion of the signal may be shunted to ground. Optionally, in the absence of the more complex circuit, the sound signal may be shunted directly to ground or even dissipated as heat by the resistors 16.

Once the filter has split the sound signal, the portion not grounded is directed to the frequency processor where it is converted to a signal useable by the frequency generator to produce a cancellation signal. The cancellation signal is then amplified and sent to a sound transducer, such as the speaker illustrated in FIG. 2 where it is converted back to sound to offer cancellation sound wave energy to reduce the sound heard outside the device.

By the above, the present invention provides a simple and effective apparatus for altering sound emitted by certain household appliances.

It will therefore be readily understood by those persons skilled in the art that the present invention is susceptible of a broad utility and application. While the present invention is described in all currently foreseeable embodiments, there may be other, unforeseeable embodiments and adaptations of the present invention, as well as variations, modifications and equivalent arrangements, that do not depart from the substance or scope of the present invention. The foregoing disclosure is not intended or to be construed to limit the present invention or otherwise to exclude such other embodiments, adaptations, variations, modifications and equivalent arrangements, the present invention being limited only by the claims appended hereto and the equivalents thereof.

I claim:

1. A sound altering apparatus for altering predetermined sound levels of a sound producing device, the sound altering apparatus comprising:

an array of piezoelectric foil sensors disposed relative to the sound producing device and operable to be influenced by sound wave energy emitted from the sound producing device and operable to convert such sound wave energy into an electric sound signal; and an electric circuit in electrical communication with the at least one piezoelectric foil sensor for receiving the electric sound signal, the electric circuit including a ground connection and being configured for shunting the electric sound signal to the ground connection, thereby reducing sound heard outside the sound producing device, wherein the sound producing device is a dishwasher having a pump and a dishwashing compartment with the array of piezoelectric foil sensors including at least one sensor disposed within the sound producing device for sensing pump sound and at least one other sensor disposed adjacent the dishwashing compartment for sensing sound produced by water circulating within the dishwashing compartment.

2. The sound altering apparatus according to claim 1 wherein the electric circuit includes at least one resistor for dissipating at least a portion of the electric sound signal as heat.

3. The sound altering apparatus according to claim 1 wherein the at least one sensor is disposed relative to the pump such that the at least one sensor is influenced by sound wave energy emitted from the pump.

4. A sound altering apparatus for altering predetermined sound levels of a sound producing device, the sound altering apparatus comprising:

an array of piezoelectric foil sensors disposed relative to the sound producing device for sensing sound wave energy emitted therefrom and converting the sound wave energy to an electric sound signal;

a first electric circuit in electrical communication with the array of piezoelectric foil sensors for receiving and analyzing the electric sound signal to determine audible frequencies that characterize the sound, and generating a first electric signal representative thereof, the electric circuit including a ground connection and being configured for shunting the at least a portion of the electric sound signal to the ground connection; and a second electric circuit including a frequency processor and generator in electrical communication with the first electric circuit for receiving the first electric signal and generating a second electric signal representative of sound-canceling frequencies;

a third electric circuit in electrical communication with the second electric circuit and including a sound transducer disposed in audible communication with the sound generating device, the third electrical circuit being configured for receiving and processing the second electrical signal to produce sound-canceling sound waves using the sound transducer, thereby reducing sound heard outside the sound producing device, wherein the sound producing device is a dishwasher having a pump and a dishwashing compartment, with the array of piezoelectric foil sensors including at least one sensor disposed relative to the sound producing device for sensing pump sound and at least one sensor disposed relative to the dishwashing compartment for sensing sound produced by water circulating within the dishwashing compartment.

5. The sound altering apparatus according to claim 4 wherein the first electric circuit includes at least one resistor for dissipating at least a portion of the first electric signal as heat.

6. The sound altering apparatus according to claim 4 wherein the at least one sensor is disposed relative to the pump such that the at least one sensor is influenced by sound wave energy emitted from the pump.

7. A sound altering apparatus for altering predetermined sound levels of a sound producing device, the sound altering apparatus comprising:

an array of piezoelectric foil sensors disposed relative to the sound generating device for sensing sound wave energy emitted therefrom and converting the sound wave energy to an electric signal;

a first electric circuit in electrical communication with the array of piezoelectric foil sensors for receiving and analyzing the electric sound signal to determine audible frequencies that characterize the sound and generating a first electric signal representative thereof, the electric circuit including a ground connection and being configured for shunting the at least a portion of the electric sound signal to the ground connection;

a second electrical circuit including a frequency processor and generator in electrical communication with the first electric circuit for receiving the first electric signal and generating a second electric signal representative of sound-canceling frequencies;

a third electric circuit in electrical communication with the second electrical circuit and including a sound transducer disposed in audible communication with the sound generating element, the third electrical circuit being configured for receiving and processing the second electrical signal to produce sound-canceling sound waves using the sound transducer; and a control circuit in electrical communication with the third electrical circuit for controlling operation thereof, the control circuit having at least two selectively engagable operational modes including a first mode for real-time monitoring of the second electrical signal for controlling the third electrical circuit responsive thereto, and a second mode for operating the third electrical circuit in conjunction with predetermined operational modes of the sound producing device, thereby reducing sound heard outside the sound producing device, wherein the sound producing device is a dishwasher having a pump and a dishwashing compartment with the array of piezoelectric foil sensors including at least one sensor disposed relative to sound producing device for sensing pump sound and at least one sensor disposed relative to the dishwashing compartment for sensing sound produced by water circulating within the dishwashing compartment.

8. The sound altering apparatus according to claim 7 wherein the at least one sensor is disposed relative to the sound producing device for sensing pump sound.

* * * * *